United States Patent [19]

Marquez

[11] Patent Number: 4,773,858

[45] Date of Patent: Sep. 27, 1988

[54] TOOTH IMPLANT

[76] Inventor: Fidencio G. Marquez, 619 Ocean Blvd., Coronado, Calif. 92118

[21] Appl. No.: 110,670

[22] Filed: Oct. 20, 1987

[51] Int. Cl.[4] .............................................. A61C 8/00
[52] U.S. Cl. ..................................... 433/173; 433/175
[58] Field of Search ................ 433/173, 176, 175, 221

[56] References Cited

U.S. PATENT DOCUMENTS

| 1,517,500 | 12/1924 | Fredericks | 433/221 |
| 3,717,932 | 2/1973 | Brainin | 433/175 |
| 4,459,111 | 7/1984 | Valen | 433/176 |

Primary Examiner—Robert Peshock
Attorney, Agent, or Firm—Ralph S. Branscomb

[57] ABSTRACT

Means and method are provided for implanting an artificial tooth in the alveolus in the jaw bone which is left when the tooth is extracted. The method comprises wrapping a thin, sheet metal base with barbed projections around the depending root portion of an artificial tooth, and pressing the root portion with the sheet metal wrapped therearound down into the alveolus, to act as an interface between the alveolus and the material of the root of the artificial tooth to securely hold the artificial tooth into the alveolus while bone material grows up around the sheet metal base and the root portion of the artificial tooth.

6 Claims, 1 Drawing Sheet

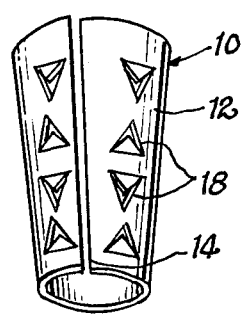
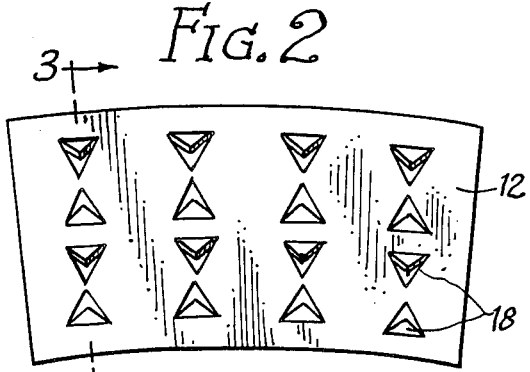
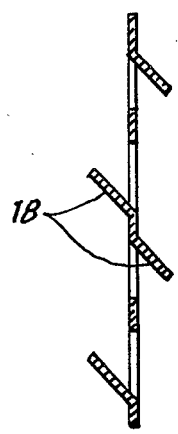
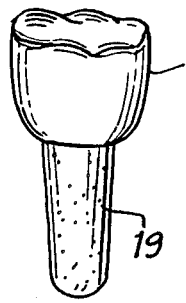
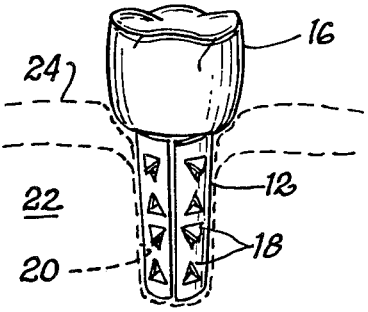
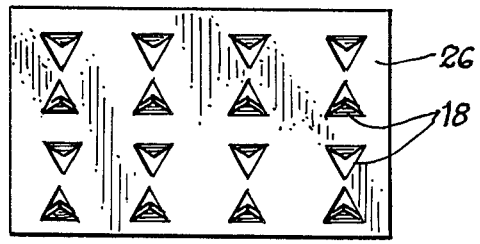
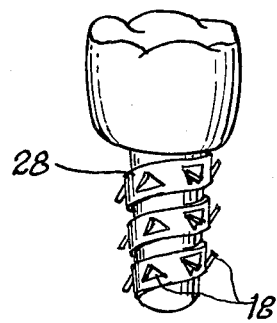

TOOTH IMPLANT

BACKGROUND OF THE INVENTION

The instant invention is in the field of dental surgery, and more particularly pertains to the implanting of artificial teeth.

Dental science will do anything possible to preserve an existing natural tooth, even if the tooth is dead, provided it is structurally intact, by means of root canals, caps, crowns, and so forth. Once the tooth is gone, bridgework may be used, or in some cases, an artificial tooth is implanted into the jawbone by drilling a hole into the jawbone, driving a post into that hole, and forming a tooth on the top of the post.

Drilling a hole in the jawbone is somewhat drastic oral surgery, and is painful. There also may be a delay involved while the post, which has been driven down into the hole in the jawbone, is engaged by the jawbone material, before the amalgam or enamel which will form the tooth can be formed around the top of the post. All of this is quite uncomfortable to the patient.

There is, therefore, a need for a technique to implant a tooth immediately after the natural tooth has been extracted, taking advantage of the natural alveolus left in the jawbone which formerly housed the root of the natural tooth. By taking advantage of the natural alveolus in this way, and by immediately mounting or implanting an artificial tooth, the trauma of dental extraction could be combined temporarily with the implantation of the artificial tooth, thus minimizing the trauma of the entire ordeal to the patient.

SUMMARY OF THE INVENTION

The instant invention fulfills the above-stated need by providing a means and a technique for implanting a slit, cylindrical metal base into the alveolus of the tooth, essentially immediately after the root of the natural tooth has been extracted and the alveolus is fresh.

The base which wraps around the depending root portion of the artificial tooth comes in several modifications, but basically comprises a cylindrical element with out-struck prongs which, at the lower portion of the base, extend outwardly and upwardly so that when the base is pushed down into the alveolus, it will compress slightly and the upwardly directed, out-struck prongs will engage in and grip the jawbone around the alveolus. A firm and secure mounting of the base will thus be formed essentially automatically upon the insertion of the base into the alveolus.

Once the depending root of the artificial tooth, wrapped with the base, has been inserted into the alveolus, the tooth is essentially ready for use, although the tooth could be favored, or possibly even not used, for a period of time to assist the bone deposits from the jawbone to further secure the artificial tooth before it is used, or at least before it is used very heavily.

Either way, as the jawbone naturally fills the alveolus as it does to replace the extracted root, it fills in around the lower portion of the base, making an extremely secure engagement, so that the longer the base is in position, the stronger it becomes.

BRIEF DESCRIPTION OF THE DRAWINGS

FIG. 1 is an isometric view of a typical, slightly conical, truncated cylindrical base;

FIG. 2 illustrate the sheet metal of the base of FIG. 1 as it would appear flattened out, but with the up-struck portions in place;

FIG. 3 is a section taken along line 3—3 of FIG. 2;

FIG. 4 is a prospective view of a typical artificial tooth showing the depending root portion;

FIG. 5 illustrates the artificial tooth of FIG. 4 with the base of FIG. 1 in place, wrapped around the root;

FIG. 6 is a flattened version of the cylindrical sheet metal of the base of FIG. 4; and FIG. 7 is yet a third embodiment of the base in which it is a helical segment of a cylinder shown wrapped around an artificial tooth root.

DETAILED DESCRIPTION OF THE PREFERRED EMBODIMENTS

The preferred embodiment of the invention is shown in FIG. 1, wherein the base 10 defines a hollow, truncated cone shaped sheath formed of rolled sheet metal, indicated at 12. The sheet metal 12 is formed to define the truncated cone such as to leave a slit 14 along the side, which will permit a certain resilience of the base member, which is desirable as it is pressed down inside the alveolus, so that it securely engages the sides of the alveolus. This also permits the unit to be size-wise adjustable to some extent, so that it will be compressible to fit in a smaller alveolus and correspondingly smaller tooth root, or could conceivably be expanded somewhat and pressed inside a larger alveolus. In the event that different sized bases would be provided, a smaller number of variations would be provided because of the size adjustability inherent in the use of the slit.

As shown in FIGS. 1 and 2, the base element needs some means of engaging the sides of the alveolus, and also for providing attachment points for the enamel amalgam of the artificial tooth, indicated at 16 in FIG. 4, in phantom. In the illustrated embodiments, these engagement means comprise upstruck triangles 18. As best shown in FIG. 3, the lower portion of the base generally has up-struck prongs or triangles 16. These project outwardly, as shown in FIG. 4, so that when the base is pressed into the alveolus 20 of the jawbone 22, just under the gum 24, these upwardly, outwardly directed prongs grip the sides of the alveolus and prevent, or help prevent, the base from being pulled upwardly. Naturally, the prong 18 that are shown are diagrammatic only and could be provided in different shape, form, density or number, the idea being that they would project and grip the sides of the alveolus and also provide openings through which the bone material above the jawbone could grow, filling the alveolus and firmly cementing the base in place as time passes.

The upper prongs of the base are preferably downwardly directed to help engage the amalgam 16 of the tooth root 19. Again, the prongs are illustrative only as innumerable variations of their shape, orientation and density could be conceived. The main idea is that both the upper portion of the base and the lower portion provide suitable engaging members for engaging the amalgam of an artificial tooth root 19 and the walls of the jawbone alveolus as shown in FIG. 4.

Another form of the base is shown, there being a straight cylindrical version shown flattened at 26 in FIG. 6, as it would appear before it is rolled into a cylinder to define the base. In any embodiment, any strong, corrosion-proof material, such as titanium alloy, could be used.

Finally, yet another form as shown in FIG. 7 wherein a helical segment 28 of a cylinder is used. Here again, both the bottom and the top portions have prongs to engage respectively in the alveolus and the artificial enamel.

Once the original tooth has been extracted, leaving the alveolus, the root wrapped with the base member is pushed into the alveolus so that the prongs engage the sides of the alveolus. However, when the base is merely inserted into the alveolus, unless it is cemented in as well, it might be somewhat loose and it might be desirable to let the bone fill in around the base in the alveolar cavity prior to heavy use of the tooth.

In either case, a secure and less traumatic technique results, and yields a strong, durable tooth that should last for many years, if not the lifetime of the user.

I claim:

1. A tooth implant sheath for anchoring an artificial tooth having a root portion dimensioned to insert into the jawbone alveolus which results from tooth extraction, said implant sheath comprising:
   (a) a generally cylindrical sheath composed of a chemically inactive sheet metal dimensioned to snugly encircle and sheath said root portion and being dimensioned to fit down into a jawbone alveolus;
   (b) said sheath having means to engage the jawbone around said alveolus; and
   (c) said sheath also having means to engage the material forming the root of said artificial tooth.

2. Structure according to claim 1 wherein said sheet metal sheath defines a continuous slit along one side to provide said sheath with dimensional adjustability and resilience.

3. Structure according the claim 1 wherein said means to engage the jawbone and means to engage the material forming the root of said artificial tooth both comprise a series of prongs struck from said generally cylindrical sheath to leave an opening at each prong for the engagement thereof by ingrowing bone tissue.

4. Structure according the claim 3 wherein said generally cylindrical sheath has an upper portion and a lower portion and the prongs of the upper portion of said sheath are generally inwardly downwardly directed and the prongs in the lower portion are generally outwardly and upwardly directed to engage the sides of an alveolus and resist removal of said sheath once inserted into said alveolus.

5. Structure according the claim 1 wherein said sheath is slightly tapered to resemble a truncated cone.

6. Structure according the claim 1 wherein said sheath comprises a helical band of a cylinder.

* * * * *